United States Patent
Yurugi et al.

(10) Patent No.: US 6,541,656 B2
(45) Date of Patent: Apr. 1, 2003

(54) PROCESS FOR PRODUCING α, β-UNSATURATED CARBOXYLIC ACID ESTERS AND CATALYST FOR USE IN SUCH PROCESS

(75) Inventors: Keiji Yurugi, Osaka (JP); Takafumi Kubo, Suita (JP)

(73) Assignee: Nippon Shokubai Company, Ltd., Osaka (JP)

( * ) Notice: Subject to any disclaimer, the term of this patent is extended or adjusted under 35 U.S.C. 154(b) by 82 days.

(21) Appl. No.: 09/778,845

(22) Filed: Feb. 8, 2001

(65) Prior Publication Data

US 2001/0034300 A1 Oct. 25, 2001

(30) Foreign Application Priority Data

Feb. 10, 2000 (JP) ........................ 2000-033272
Feb. 10, 2000 (JP) ........................ 2000-033274

(51) Int. Cl.$^7$ .............................. C07C 67/26
(52) U.S. Cl. ................. 560/209; 560/93; 560/200
(58) Field of Search .................. 560/205, 209, 560/224, 200, 93

(56) References Cited

U.S. PATENT DOCUMENTS 5,191,104 A * 3/1993 King .................... 558/260

FOREIGN PATENT DOCUMENTS

| CA | 2140304 | * 7/1995 | ........... C07C/69/54 |
|----|---------|----------|----------------------|
| DE | 197 34 906 A1 | 2/1999 | |
| EP | 0 738 703 A2 | 10/1996 | |
| EP | 0 965 382 A1 | 12/1999 | |
| JP | 62-44537 | 9/1987 | |
| JP | 2-71841 | 3/1990 | |
| JP | 3-242242 | 10/1991 | |
| JP | 5-170688 | 7/1993 | |
| JP | 6-88944 | 11/1994 | |
| JP | 7-227540 | 8/1995 | |
| JP | 8-169860 | 7/1996 | |
| JP | 8-169861 | 7/1996 | |
| JP | 8-268919 | 10/1996 | |
| JP | 8-323200 | 12/1996 | |
| JP | 2636079 | 4/1997 | |
| JP | 9-227-451 | 9/1997 | |
| JP | 10-99693 | 4/1998 | |
| JP | 10-137592 | 5/1998 | |
| JP | 10-158384 | 6/1998 | |
| JP | 11-71328 | 3/1999 | |
| JP | 11071328 A | 3/1999 | |
| JP | 11-114417 | 4/1999 | |
| JP | 11-319556 | 11/1999 | |
| JP | 2000-15094 | 1/2000 | |
| JP | 2000-15095 | 1/2000 | |
| JP | 2000-16958 | 1/2000 | |
| JP | 2000016958 | 1/2000 | |
| JP | 2000-297062 | * 10/2000 | ........... C07C/67/26 |

OTHER PUBLICATIONS

Junzo Otera et al, "A Convenient Synthesis of Glycidyl Esters (2,3–Epoxypropyl Alkanoates)", Syn., (1986), pp. 1019–1020.*
Junzo Otera et al. "Highly Regioselective Ring Opening of Epoxides with Alcohols Catalyzed By Organotin Phosphate Condensates", Tet. Lett., vol. 26 (1985), pp. 3219–3222.*
Yaoxian Li et al, "Synthesis of β–hydroxypropyl carboxylic acid esters", Chemical Abstracts 119:72223 [Julin Daxue Ziran Kexue Xuebao, (1992), pp. 109–111].*

* cited by examiner

Primary Examiner—Paul J. Killos
(74) Attorney, Agent, or Firm—Connolly Bove Lodge & Hutz LLP

(57) ABSTRACT

Economical and efficient processes for producing an α, β-unsaturated carboxylic acid heterocycle-inserted ester and an α,β-unsaturated carboxylic acid polyheteroalkylene ester as well as a catalyst suited for use in economically and efficiently producing an α,β-unsaturated carboxylic acid ester are provided.

The invention provides
(1) a process for producing an α,β-unsaturated carboxylic acid ester which comprises reacting an α,β-unsaturated carboxylic acid ester with a heterocyclic compound,
(2) a process for producing an α,β-unsaturated carboxylic acid ester
which comprises reacting an α,β-unsaturated carboxylic acid with a heterocyclic compound
in the presence of a polymerization inhibitor and a metal oxide catalyst, and
(3) a catalyst for the production of an α,β-unsaturated carboxylic acid ester
comprising a metal oxide.

24 Claims, No Drawings

PROCESS FOR PRODUCING α, β-UNSATURATED CARBOXYLIC ACID ESTERS AND CATALYST FOR USE IN SUCH PROCESS

FIELD OF THE INVENTION

The present invention relates to a process for producing α,β-unsaturated carboxylic acid heterocycle-inserted esters or α,β-unsaturated carboxylic acid polyheteroalkylene esters. More particularly, it relates to a process for producing α, β-unsaturated carboxylic acid heterocycle-inserted esters which comprises reacting and α,β-unsaturated carboxylic acid esters with heterocyclic compounds, a process for producing α, β-unsaturated carboxylic acid polyheteroalkylene esters which comprises reacting α,β-unsaturated carboxylic acids with heterocyclic compounds in the presence of polymerization inhibitors and metal oxide catalysts, and a catalyst which can be used with advantage in such processes.

PRIOR ART

α,β-Unsaturated carboxylic acid heterocycle-inserted esters and α,β-unsaturated carboxylic acid polyheteroalkylene esters are polymerizable and therefore are useful compounds widely usable on a commercial scale as raw materials for the synthesis of perfumes and of medicinals or agrochemicals, as organic synthetic intermediates, or as polymerizable materials and so forth. For example, polyoxyethylene monomethyl ether (meth)acrylates are known as such α,β-unsaturated carboxylic acid heterocycle-inserted esters, and 2-hydroxyethyl (meth) acrylate is known as such α,β-unsaturated carboxylic acid polyheteroalkylene esters.

It is known that polyoxyethylene monomethyl ether (meth) acrylates can be produced by synthesizing polyoxyethylene monoalkyl ethers from methanol and ethylene oxides and subjecting the polyoxyethylene monomethyl ether to esterification or transesterification with (meth) acrylic acids or (meth)acrylate esters. However, such process for producing polyoxyethylene monomethyl ether (meth)acrylates is not satisfactory from the commercial practicing view points since it comprises two reaction steps and allows the formation of an equimolar amount of water or the corresponding alcohol as a reaction byproduct.

For producing 2-hydroxyethyl (meth)acrylates, a process is known which comprises reacting (meth)acrylic acids, which are α,β-unsaturated carboxylic acids, with an ethylene oxide, which is a heterocyclic compound, in the presence of one of various catalysts, such as various amines, quaternary ammonium salts, trivalent iron compounds, chromium compounds, silver or mercury and metal compounds derived from α,β-unsaturated carboxylic acids. Such process for producing 2-hydroxyethyl (meth)acrylates, however, has problems: it is difficult to control the number of moles of an ethylene oxide, which is a heterocyclic compound, to be added, therefore the distribution of numbers of moles of ethylene oxides added becomes broad. Furthermore, dimeric diesters resulting from the addition of α,β-unsaturated carboxylic acids to both termini of the polyoxyalkylene are also formed and, when used for polymerization purposes, in particular, the diesters serve as crosslinking agents, causing a problem of gelation, among others.

Japanese Kokai Publication Hei-11-71328 discloses that a process for producing aliphatic polyoxyalkylene alkyl ethers each having a specific chemical structure which comprises inserting alkylene oxides directly into fatty acid alkyl esters in the presence of composite metal oxide catalysts can produce the desired products in an efficient and economical manner. Further, Japanese Kokai Publication 2000-16958 discloses that a process for producing alkylene oxide adducts which comprises reacting active hydrogen-containing organic compounds with alkylene oxides in the presence of powder-form magnesium oxide catalysts having a specified specific surface area can give the alkylene oxide adducts low in byproduct contents. However, the publications cited above disclose nothing about the production of α,β-unsaturated carboxylic acid heterocycle-inserted esters or α, β-unsaturated carboxylic acid polyheteroalkylene esters, which are polymerizable and therefore are compounds of commercial importance for use in a wide range. Thus, there has been room for investigation in search for an appropriate process for producing such α,β-unsaturated carboxylic acid heterocycle-inserted esters or α,β-unsaturated carboxylic acid polyheteroalkylene esters.

SUMMARY OF THE INVENTION

In view of the above-mentioned state of the art, it is an object of the present invention to provide a process for producing an α,β-unsaturated carboxylic acid heterocycle-inserted ester economically and efficiently. Another object is to provide an economical and efficient process for producing an α,β-unsaturated carboxylic acid polyheteroalkylene ester showing a sharp distribution of numbers of moles of the heterocyclic compounds added and containing almost no α,β-unsaturated carboxylic acid diesters. A further object is to provide a catalyst suited for use in producing an α,β-unsaturated carboxylic acid ester in an economical and efficient manner.

The present inventors conducted intensive investigations to provide an economical process for producing an α,β-unsaturated carboxylic acid heterocycle-inserted ester. As a result, they found in the first place that, by reacting an α,β-unsaturated carboxylic acid ester with a heterocyclic compound, it is possible to produce an α,β-unsaturated carboxylic acid heterocycle-inserted ester in an economical and efficient manner since the process is curtailed and the formation of the byproducts water or alcohol is suppressed. Paying attention to the above facts, they thought that such effects might be produced more reliably if the chemical structures of the heterocyclic compounds are restricted to a specific one. They also found that when the reactions are carried out in the presence of a metal oxide catalyst, the desired products can be produced more economically and more efficiently and that when polymerization inhibitors are used and/or the oxygen concentration in the gaseous phase in the reactor employed in carrying out the reaction is specified, the polymerization of α,β-unsaturated carboxylic acid esters or α,β-unsaturated carboxylic acid heterocycle-inserted esters can be suppressed and the above effects can fully be expressed.

Thus, the invention provides a process for producing an α,β-unsaturated carboxylic acid ester which comprises the step of reacting an α,β-unsaturated carboxylic acid ester of the general formula (1):

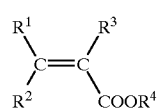

wherein $R^1$, $R^2$ and $R^3$ are the same or different and each represents a hydrogen atom or an organic residue and $R^4$ represents an organic residue, with a heterocyclic compound of the general formula (2):

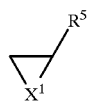

(2)

wherein $R^5$ represents a hydrogen atom or an organic residue and $X^1$ represents O, S or NH,
to give an α,β-unsaturated carboxylic acid ester of the general formula (3):

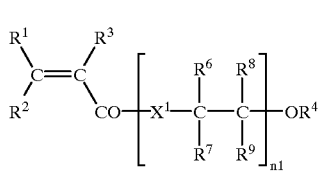

(3)

wherein $R^1$, $R^2$ and $R^3$ are the same or different and each represents a hydrogen atom or an organic residue, $R^4$ represents an organic residue, one of $R^6$, $R^7$, $R^8$ and $R^9$ represents $R^5$ and the remaining three each represents a hydrogen atom, $X^1$ represents O, S or NH and n1 represents a positive integer one or more.

The present inventors also made intensive studies to provide an economical process for producing an α,β-unsaturated carboxylic acid polyheteroalkylene ester showing a sharp distribution of numbers of moles of the heterocyclic compounds added and containing almost no α,β-unsaturated carboxylic acid diesters and, as a result, found that an α,β-unsaturated carboxylic acid polyheteroalkylene ester can be produced economically by reacting an α,β-unsaturated carboxylic acid with a heterocyclic compound in the presence of a polymerization inhibitor and a metal oxide catalyst. They thought that such effects might be obtained with greater certainty if the chemical structure of the heterocyclic compound be restricted to a specific one, like the case mentioned above. They also found that when the oxygen concentration in the gaseous phase space in the reactor employed in carrying out the reaction is specified, the same effects as mentioned above can be produced. Based on these findings, the invention has now been completed.

Thus, the invention also provides a process for producing an α,β-unsaturated carboxylic acid ester
which comprises the step of reacting an α,β-unsaturated carboxylic acid of the general formula (4):

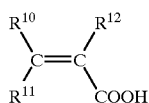

(4)

wherein $R^1$, $R^2$ and $R^3$ are the same or different and each represents a hydrogen atom or an organic residue,
with a heterocyclic compound of the general formula (5):

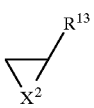

(5)

wherein $R^{13}$ represents a hydrogen atom or an organic residue and $X^2$ represents O, S or NH, in the presence of a polymerization inhibitor and a metal oxide catalyst,
to give an α,β-unsaturated carboxylic acid ester of the general formula (6):

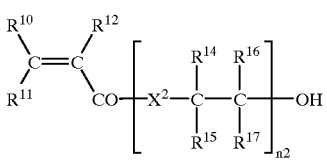

(6)

wherein $R^{10}$, $R^{11}$ and $R^{12}$ are the same or different and each represents a hydrogen atom or an organic residue, one of $R^{14}$, $R^{15}$, $R^{16}$ and $R^{17}$ represents $R^{13}$ and the remaining three each represents a hydrogen atom, $X^2$ represents O, S or NH and n2 represents a positive integer one or more.

In the following, the present invention is described in detail.

DETAILED DESCRIPTION OF THE INVENTION

The process of the invention for producing α,β-unsaturated carboxylic acid esters comprises the step of reacting α,β-unsaturated carboxylic acid esters represented by the above general formula (1) with heterocyclic compounds represented by the above general formula (2) to give α,β-unsaturated carboxylic acid heterocycle-inserted esters represented by the above general formula (3) Such process for producing α,β-unsaturated carboxylic acid esters may or may not comprise another step or steps other than the above reaction step. The α,β-unsaturated carboxylic acid esters in the practice of the invention are also referred to as α,β-unsaturated carboxylic acid heterocycle-inserted esters.

The above step may be carried out in the liquid phase or the gas phase, however it is preferably carried out in the liquid phase in the present invention. Particularly, when $X^1$ represents O, the step is preferably carried out in the liquid phase. This is because the reaction in the gas phase in the presence of metal oxide catalysts causes to occur polyalkylene glycols due to the polymerization of heterocyclic compounds and therefor the deactivation of the catalysts and/or closing the reactors is likely to occur in this system.

The α,β-unsaturated carboxylic acid esters of the general formula (1), which are used as starting materials in the practice of the invention, are not particularly restricted but may be any of those compounds of the general formula (1) in which the substituents represented by $R^1$, $R^2$ and $R^3$ in that formula are the same or different and each is a hydrogen atom or an organic residue and the substituent represented by $R^4$ is an organic residue.

In the present specification, the term "organic residue" as used referring to a compound(s) represented by a general formula means a group bonded to the basic structure constituting the compound(s) and constituted of atoms other than metal atoms as essential constituents. As the atomic groups constituted of atoms other than metal atoms as essential constituents, there may be mentioned, for example, hydrocarbon groups containing 1 to 20 carbon atoms and nitrogen atom-containing groups such as those mentioned below.

The organic residues represented by $R^1$, $R^2$ or $R^3$ are not particularly restricted but include, among others, straight, branched or cyclic, saturated and/or unsaturated alkyl groups containing 1 to 20 carbon atoms, hydroxyalkyl groups containing 1 to 10 carbon atoms, alkoxyalkyl groups containing 1 to 10 carbon atoms, haloalkyl groups containing 1 to 10 carbon atoms, acyloxy groups containing 1 to 10 carbon atoms, acyloxy alkyl groups containing 1 to 20 carbon atoms, aryl groups, which may optionally have a substituent(s), a carboxyl group, carboxylic acid ester groups represented by -COOR (R being the same organic residue as $R^4$) and amido groups. Among them, saturated and/or unsaturated alkyl groups containing 1 to 8 carbon atoms, carboxylic acids and carboxylic acid esters are suited for use.

The organic residues represented by $R^4$ are not particularly restricted but include, among others, straight, branched or cyclic, saturated and/or unsaturated alkyl groups containing 1 to 20 carbon atoms, hydroxyalkyl groups containing 1 to 10 carbon atoms, alkoxyalkyl groups containing ito 10 carbon atoms, haloalkyl groups containing 1 to 10 carbon atoms, and aryl groups, which may optionally have a substituent(s). Among them, saturated and/or unsaturated alkyl groups containing 1 to 8 carbon atoms are suited for use.

Typical examples of the above $\alpha,\beta$-unsaturated carboxylic acid esters of the general formula (1) specifically include, but are not particularly limited to the esters in the following:

(meth)acrylate esters such as methyl (meth)acrylate, ethyl (meth)acrylate, propyl (meth)acrylate, butyl (meth)acrylate, pentyl (meth)acrylate, hexyl (meth)acrylate, cyclohexyl (meth)acrylate, heptyl (meth)acrylate, octyl (meth)acrylate, 2-ethylhexyl (meth)acrylate, nonyl (meth)acrylate, decyl (meth)acrylate, vinyl (meth)acrylate, phenyl (meth)acrylate, benzyl (meth)acrylate, cyclohexyl methyl (meth)acrylate, 4-methylcyclohexyl methyl (meth)acrylate, 2-hydroxyethyl (meth)acrylate, 2-hydroxypropyl (meth)acrylate, 2-hydroxyisopropyl (meth)acrylate, 3-hydroxypropyl (meth)acrylate, and 4-hydroxybutyl (meth)acrylate;

maleic acid esters such as dimethyl maleate, diethyl maleate, dipropyl maleate, dibutyl maleate, dipentyl maleate, dihexyl maleate, dicyclohexyl maleate, diheptyl maleate, -dioctyl maleate, di-2-ethylhexyl maleate, dinonyl maleate, didecyl maleate, divinyl maleate, diphenyl maleate, dibenzyl maleate, monomethyl maleate, monoethyl maleate, monopropyl maleate, monobutyl maleate, monopentyl maleate, monohexyl maleate, monocyclohexylmaleate, monoheptylmaleate, monooctyl maleate, mono-2-ethylhexyl maleate, monononyl maleate, monodecyl maleate, monovinyl maleate, monophenyl maleate, monobenzyl maleate, methyl ethyl maleate, ethyl butyl maleate, methyl propyl maleate and methyl butyl maleate; fumaric acid esters such as dimethyl fumarate, diethyl fumarate, dipropyl fumarate, dibutylfumarate, dipentylfumarate, dihexylfumarate, dicyclohexyl fumarate, diheptyl fumarate, dioctyl fumarate, di-2-ethylhexyl fumarate, dinonyl fumarate, didecyl fumarate, divinyl fumarate, diphenyl fumarate, dibenzyl fumarate, monomethyl fumarate, monoethyl fumarate, monopropyl fumarate, monobutyl fumarate, monopentyl fumarate, monohexyl fumarate, monocyclohexyl fumarate, monoheptyl fumarate, monooctyl fumarate, mono-2-ethylhexyl fumarate, monononyl fumarate, monodecyl fumarate, monovinyl fumarate, monophenyl fumarate, monobenzylfumarate, methylethylfumarate, ethylbutyl fumarate, methyl propyl fumarate and methyl butyl fumarate; itaconic acid esters such as dimethyl itaconate, diethyl itaconate, dipropyl itaconate, dibutyl itaconate, dipentyl itaconate, dihexyl itaconate, dicyclohexyl itaconate, diheptyl itaconate, dioctyl itaconate, di-2-ethylhexyl itaconate, dinonyl itaconate, didecyl itaconate, divinyl itaconate, diphenyl itaconate, dibenzyl itaconate, monomethyl itaconate, monoethyl itaconate, monopropyl itaconate, monobutyl itaconate, monopentyl itaconate, monohexyl itaconate, monocyclohexyl itaconate, monoheptyl itaconate, monooctyl itaconate, mono-2-ethylhexyl itaconate, monononyl itaconate, monodecyl itaconate, monovinyl itaconate, monophenyl itaconate, monobenzyl itaconate, methyl ethyl itaconate, ethyl butyl itaconate, methyl propyl itaconate and methyl butyl itaconate;

methylenemalonic acid esters such as dimethyl methylenemalonate, diethyl methylenemalonate, dipropyl methylenemalonate, dibutyl methylenemalonate, dipentyl methylenemalonate, dihexyl methylenemalonate, dicy=lohexyl methylenemalonate, diheptyl methylenemalonate, dioctyl methylenemalonate, di-2-ethylhexyl methylenemalonate, dinonyl rmethylenemalonate, didecyl methylenemalonate, divinyl methylenemalonate, diphenyl methylenemalonate, dibenzyl methylenemalonate, monomethyl methylenemalonate, monoethyl methylenemalonate, monopropyl methylenemalonate, monobutyl methylenemalonate, monopentyl methylenemalonate, monohexyl methylenemalonate, monocyclohexyl methylenemalonate, monoheptyl methylenemalonate, monooctyl methylenemalonate, mono-2-ethylhe x yl methylenemalonate, monononyl methylenemalonate, monodecyl methylenemalonate, monovinyl methylenemalonate, monophenyl methylenemalonate, monobenzyl methylenemalonate, methyl ethyl methylenemalonate, ethyl butyl methylenemalonate, methyl propyl methylenemalonate and methyl butyl methylenemalonate;

$\alpha$-hydroxyalkylacrylate esters such as methyl $\alpha$-hydroxymethylacrylate, ethyl $\alpha$-hydroxymethylacrylate, propyl $\alpha$-hydroxymethylacrylate, butyl $\alpha$-hydroxymethylacrylate, ethylhexyl $\alpha$-hydroxymethylacrylate, methyl $\alpha$-(1-hydroxyethyl)acrylate, ethyl $\alpha$-(1-hydroxyethyl)acrylate, propyl $\alpha$-(1-hydroxyethyl)acrylate, butyl $\alpha$-(1-hydroxyethyl)acrylate and ethylhexyl $\alpha$-(1-hydroxyethyl)acrylate; $\alpha$-haloalkylacrylate esters such as methyl $\alpha$-chloromethylacrylate, ethyl $\alpha$-chloromethylacrylate, propyl$\alpha$-chloromethylacrylate, butyl $\alpha$-chloromethylacrylate, ethylhexyl $\alpha$-chloromethylacrylate, methyl $\alpha$-(1-chloroethyl)acrylate, ethyl $\alpha$-(1-chloroethyl)acrylate, propyl $\alpha$-(1-chloroethyl)acrylate, butyl $\alpha$-(1-chloroethyl)acrylate, ethylhexyl $\alpha$-(1-chloroethyl)acrylate, methyl $\alpha$-bromomethylacrylate, ethyl $\alpha$-bromomethylacrylate, propyl $\alpha$-bromomethylacrylate, butyl $\alpha$-bromomethylacrylate, ethylhexyl $\alpha$-bromomethylacrylate, methyl $\alpha$-(1-bromoethyl)acrylate, ethyl $\alpha$-(1-bromoethyl)acrylate, propyl$\alpha$-(1-bromoethyl)acrylate, butyl $\alpha$-(1-bromoethyl)acrylate and ethylhexyl $\alpha$-(1-bromoethyl)acrylate; $\alpha$-acyloxyalkylacrylate esters such as methyl $\alpha$-acetoxymethylacrylate, ethyl $\alpha$-acetoxymethylacrylate, propyl$\alpha$-acetoxymethylacrylate, butyl $\alpha$-acetoxymethylacrylate and ethylhexyl $\alpha$-acetoxymethylacrylate;

cinnamate esters such as methyl cinnamate, ethyl cinnamate, propyl cinnamate, butyl cinnamate, phenyl cinnamate and benzyl cinnamate; crotonate esters such as methyl crotonate, ethyl crotonate, propyl crotonate, butyl crotonate, phenyl crotonate and benzyl crotonate;

β-alkylacrylate esters such as methyl β-ethylacrylate, ethyl β-ethylacrylate, propyl β-ethylacrylate, butyl β-ethylacrylate, phenyl β-ethylacrylate, benzyl β-ethylacrylate, methyl β-propylacrylate, ethyl β-propylacrylate, propyl β-propylacrylate, butyl β-propylacrylate, phenyl β-propylacrylate and benzyl β-propylacrylate; β-alkoxyacrylate esters such as methyl β-methoxyacrylate, ethyl β-methoxyacrylate, propyl β-methoxyacrylate, butyl β-methoxyacrylate, phenyl β-methoxyacrylate, benzyl β-methoxyacrylate, methyl β-ethoxyacrylate, ethyl β-ethoxyacrylate, propyl β-ethoxyacrylate, butyl β-ethoxyacrylate, phenyl β-ethoxyacrylate and benzyl β-ethoxyacrylate; and α-acetamidoacrylate esters such as methyl α-acetamidoacrylate, ethyl α-acetamidoacrylate, propyl α-acetamidoacrylate, butyl α-acetamidoacrylate, phenyl α-acetamidoacrylate and benzyl α-acetamidoacrylate.

These may be used singly or two or more of them may be used combinedly.

Among typical examples of the above α,β-unsaturated carboxylic acid esters of the general formula (1), appropriately used are methyl (meth)acrylate, ethyl (meth)acrylate, propyl (meth)acrylate, butyl (meth)acrylate, 2-ethylhexyl (meth)acrylate, vinyl (meth)acrylate, phenyl (meth)acrylate, benzyl (meth)acrylate, cyclohexyl (meth)acrylate, cyclohexyl methyl (meth)acrylate, 4-methylcyclohexyl methyl (meth)acrylate, 2-hydroxyethyl (meth)acrylate, 2-hydroxypropyl (meth)acrylate, 2-hydroxyisopropyl (meth)acrylate, 3-hydroxypropyl (meth)acrylate, 4-hydroxybutyl (meth)acrylate, dimethyl maleate, diethyl maleate, dipropyl maleate, dibutyl maleate, di-2-ethylhexyl maleate, dimethyl fumarate, diethyl fumarate, dipropyl fumarate, dibutyl fumarate, di-2-ethylhexyl fumarate, dimethyl itaconate, diethyl itaconate, dipropyl itaconate, dibutyl itaconate, di-2-ethylhexyl itaconate, methyl α-hydroxymethylacrylate, ethyl α-hydroxymethylacrylate, propyl α-hydroxymethylacrylate, butyl α-hydroxymethylacrylate, 2-ethylhexyl α-hydroxymethylacrylate, methyl ce-acetoxymethylacrylate; methyl cinnamate, ethyl cinnamate, propyl cinnamate, butyl cinnamate, methyl crotonate, ethyl crotonate, propyl crotonate and butyl crotonate.

The heterocyclic compounds of the general formula (2), which are used as another starting material in the practice of the present invention are not particularly restricted but may be any of those compounds of the general formula (2) in which the substituent represented by $R^5$ is a hydrogen atom or an organic residue and the substituent represented by $X^1$ is O, S or NH.

The organic residues represented by $R^5$ are not particularly restricted but include, among others, straight, branched or cyclic, saturated and/or unsaturated alkyl groups containing 1 to 10 carbon atoms, hydroxyalkyl groups containing 1 to 5 carbon atoms, haloalkyl groups containing 1 to 5 carbon atoms and aryl groups.

Typical examples of the above heterocyclic compounds of the general formula (2) are not particularly restricted but specifically include ethylene oxide, propylene oxide, 1,2-butyleneoxide, 2,3-butyleneoxide, epoxybutene, glycidol, epichlorohydrin, epibromohydrin, styrene oxide, ethylene imine and ethylene sulfide. These may be used singly or two or more them may be used combinedly. Among them, ethylene oxide and propylene oxide are preferably used.

The mole ratio between the above α,β-unsaturated carboxylic acid esters of the general formula (1) and the above heterocyclic compounds of the general formula (2) in the reaction therebetween is not particularly restricted but is determined according to the desired number of moles of the heterocyclic compounds to be added. When the desired mean number of moles to be added is 2, for instance, the mole ratio of α,β-unsaturated carboxylic acid esters/heterocyclic compounds should be around ½.

The α, β-unsaturated carboxylic acid esters of the general formula (1) andthe heterocyclic compounds of the general formula (2) may be added to the reaction system each all at once at the beginning of the reaction, or either one of them may be added to the reaction system continuously or intermittently, or both may be added to the reaction system continuously or intermittently. Among them, the charging of both all at once or the addition of the heterocyclic compounds to the reaction system continuously or intermittently is preferred.

In the step of reacting the above α, β-unsaturated carboxylic acid esters of the general formula (1) with the heterocyclic compounds of the general formula (2), metal oxides are preferably used as a catalyst. Thus, it is preferable from the yield viewpoint to carry out the reaction in the practice of the invention in the presence of metal oxide catalysts.

Since the starting material α, β-unsaturated carboxylic acid esters of the general formula (1) and the product α, β-unsaturated carboxylic acid heterocycle-inserted esters of the general formula (3) are radical-polymerizable compounds, it is preferable from the yield viewpoint to carry out the reaction in the above reaction step in the presence of polymerization inhibitors, which inhibit the radical polymerization of such compounds. Further, injection of molecular oxygen-containing gas, molecular nitrogen oxide-containing gas, molecular nitrogen dioxide-containing gas into the reaction gas phase and/or liquid phase contributes to the inhibition of the polymerization.

The metal oxides and polymerization inhibitors, which can be used in the above reaction step, will be mentioned later herein.

The α,β-unsaturated carboxylic acid heterocycle-inserted esters in the practice of the present invention are represented by the above general formula (3) and, in that formula, $R^1$, $R^2$, $R^3$ and $R^4$ are as defined above referring to the general formula (1). $R^5$ and $X^1$ are as defined hereinabove referring to the general formula (2). One of $R^6$, $R^7$, $R^8$ and $R^9$ represents $R^5$ and the remaining three each represents a hydrogen atom. The n1 represents a positive integer of not less than 1.

In another aspect of the invention, the process for producing α,β-unsaturated carboxylic acid esters comprises the step of reacting α,β-unsaturated carboxylic acids represented by the above general formula (4) with heterocyclic compounds represented by the above general formula (5) in the presence of polymerization inhibitors and metal oxide catalysts to give α,β-unsaturated carboxylic acid polyheteroalkylene esters represented by the above general formula (6). Such process for producing α,β-unsaturated carboxylic acid esters may or may not comprise a further step or steps other than the above reaction step. Such α,β-unsaturated carboxylic acid esters producible according to the present invention are referred to as α,β-unsaturated carboxylic acid polyheteroalkylene esters as well.

The above step may be carried out in the liquid phase or the gas phase, however it is preferably carried out in the liquid phase in the present invention. Particularly, when $X^2$ represents O, the step is preferably carried out in the liquid phase. This is because the reaction in the gas phase in the presence of metal oxide catalysts causes to occur polyalkylene glycols due to the polymerization of heterocyclic compounds and therefor the deactivation of the catalysts or closing the reactors is likely to occur in this system.

In the above reaction step, the reaction is carried out in the presence of polymerization inhibitors and metal oxide catalysts. When the reaction is carried out in the presence of polymerization inhibitors, the starting material α,β-unsaturated carboxylic acids of the general formula (4) and the product α,β-unsaturated carboxylic acid polyheteroalkylene esters of the general formula (6), which are radical-polymerizable compounds, are inhibited from radical polymerization and therefore the yield is improved. Further, injection of molecular oxygen-containing gas, molecular nitrogen oxide-containing gas, molecular nitrogen dioxide-containing gas into the reaction gas phase and/or liquid phase contributes to the inhibition of the polymerization. Furthermore, when the reaction is conducted in the presence of metal oxide catalysts, the yield is more improved.

The α,β-unsaturated carboxylic acids of the general formula (4), which are to be used as a starting material in the practice of the invention, are not particularly restricted but maybe any of those compounds of the general formula (4) in which the substituents represented by $R^{10}$, $R^{11}$, and $R^{12}$ are the same or different and each is a hydrogen atom or an organic residue. Referring to $R^{10}$, $R^{11}$ and $R^{12}$, the organic residues are not particularly restricted but include, for instance, the same ones as mentioned hereinbefore referring to $R^1$, $R^2$ and $R^3$.

Typical examples of the α,β-unsaturated carboxylic acids of the general formula (4) specifically include, but are not particularly limited to (meth) acrylic acid, maleic acid, maleic acidmonoesters, fumaricacid, fumaricacidmonoesters, itaconic acid, itaconic acid monoesters, methylenemalonic acid, methylenemalonic acid monoesters, α-hydroxymethylacrylic acid, α-(1-hydroxyethyl)acrylic acid, α-chloromethylacrylic acid, α-(1-chloroethyl)acrylic acid, α-bromomethylacrylic acid, α-(1-bromoethyl)acrylic acid, α-acetoxymethylacrylic acid, cinnamic acid, crotonic acid, α-acetamidoacrylic acid, β-ethyl (meth) acrylic acid, β-propyl (meth) acrylic acid, β-methoxy(meth)acrylic acid and β-ethoxy(meth)acrylic acid. These may be used singly or two or more of them may be used combinedly. Among them, preferably used are (meth)acrylic acid, maleic acid, maleic acid monoesters, fumaric acid, fumaric acid monoesters, itaconic acid, itaconic acid monoesters, cinnamic acid, crotonic acid.

The heterocyclic compounds of the general formula (5), which are to be used as a starting material according to the invention, are not particularly restricted but any of those compounds of the general formula (5) in which the substituent represented by $R^{13}$ is a hydrogen atom or an organic residue and the substituent represented by $X^2$ is O, S or NH.

Referring to $R^{13}$, the organic residue is not particularly restricted but includes the same ones as mentioned hereinabove referring to $R^5$. Typical examples of the heterocyclic compounds of the general formula (5) are not particularly restricted but include, for example, the same ones as those typical examples given hereinabove of the heterocyclic compounds of the general formula (2).

The mole ratio between the above α,β-unsaturated carboxylic acids of the general formula (4) and the above heterocyclic compounds of the general formula (5) in the reaction therebetween is not particularly restricted but is determined according to the desired number of moles of the heterocyclic compounds to be added. When the desired mean number of moles to be added is 2, for instance, the mole ratio of α,β-unsaturated carboxylic acids/heterocyclic compounds should be around ½.

The α,β-unsaturated carboxylic acids of the general formula (4) andthe heterocyclic compounds of the general formula (5) may be added to the reaction system each all at once at the beginning of the reaction, or either one of them may be added to the reaction system continuously or intermittently, or both may be added to the reaction system continuously or intermittently. Among them, the charging of both all at once or the addition of the heterocyclic compound to the reaction system continuously or intermittently is preferred.

The α,β-unsaturated carboxylic acid polyheteroalkylene esters producible according to the invention are of the general formula (6) given hereinabove, in which $R^{10}$, $R^{11}$ and $R^{12}$ are as are defined above referring to the general formula (4) and x are as defined above referring to the general formula (5), one of $R^{14}$, $R^{15}$, $R^{16}$ and $R^{17}$ represents $R^{13}$ and the remaining three each represents a hydrogen atom and n2 represents a positive integer not less than 1.

The metal oxide catalysts and polymerization inhibitors which can be used in the practice of the invention, namely the metal oxide catalysts and polymerization inhibitors which can be used in the step of reacting the α,β-unsaturated carboxylic acid esters of the general formula (1) with the heterocyclic compounds of the general formula (2) or in the step of reacting the α,β-unsaturated carboxylic acids of the general formula (4) with the heterocyclic compounds of the general formula (5), are described below.

The metal oxide catalysts are not particularly restricted but include, among others, beryllium oxide, magnesium oxide, calcium oxide, strontium oxide, barium oxide, radium oxide, chromium oxide, zirconium oxide, iron oxides and cobalt oxide. These may be used singly or two or more of them may be used combinedly. Among those metal oxides, magnesium oxide is particularly preferred.

In the practice of the invention, it is more preferred that the above metal oxides are composite metal oxides. Said composite metal oxides are not particularly restricted but, when magnesium oxides are taken as an example, there may be mentioned the calcination products derived from coprecipitates of magnesium hydroxides with metal hydroxides such as aluminum magnesium hydroxide; calcined magnesium oxide with at least one metal ion selected from among $Al^{3+}$, $Ga^{3+}$, $Zr^{4+}$, $Ti^{4+}$, $Si^{4+}$, $In^{3+}$, $Tl^{3+}$, $Co^{3+}$, $Ni^{3+}$, $Sc^{3+}$, $La^{3+}$, $Fe^{2+}$, $Cr^{3+}$, $Cu^{2+}$, and $Mn^{2+}$ added; calcined hydrotalcite and so forth. These may be used singly or two or more of them may be used combinedly. Among these composite metal oxides, Mg-Al based composite metal oxides are particularly preferred.

The atom ratio (Be, Mg, Ca, Sr, Ba, Ra, Cr, Zr, Fe and Co)/(Al, Ga, Zr, Ti, Si, In, Tl, Co, Ni, Sc, La, Fe, Cr, Cu and Mn) in the above composite metal oxides is not particularly restricted but is preferred in the range of 0.1 to 5, more preferred in the range of 0.5 to 4, particularly preferred in the range of 1 to 3. The above atom ratio range is preferred from the yield viewpoint. In the above formula of the atom ratio range, the same kind atom is not simultaneously used for the numerator and the denominator.

The calcination temperature in preparing the above composite metal oxides is not particularly restricted but is preferred in the range of 200 to 1000° C., more preferred in the range of 300 to 950° C., particularly preferred in the range of 400 to 800° C. The calcination time is not particularly restricted but is preferred in the range of 30 to 400 minutes, more preferred in the range of 30 to 300 minutes, particularly preferred in the range of 60 to 250 minutes. The above calcination temperature and calcination time ranges are preferred from the viewpoints of catalyst activation, which influences the yield, and of crystal structure retention.

In the practice of the invention, the above metal oxides are preferably surface-modified with metal hydroxides and/or metal alkoxides. For example, the metal oxide catalysts or composite metal oxide catalysts can be surface-modified with metal hydroxides and/or metal alkoxides as necessary to give the corresponding modified metal oxide catalysts or modified composite metal oxide catalysts, and such modified metal oxide catalysts or modified composite metal oxide catalysts can be used. The metal hydroxides are not particularly restricted but include, among others, alkali metal hydroxides such as lithium hydroxide, sodium hydroxide and potassium hydroxide; alkaline earth metal hydroxides such as calcium hydroxide and magnesium hydroxide. The metal alkoxides are not particularly restricted but include, among others, alkali metal alkoxides such as sodium methoxide, sodium ethoxide, sodium butoxide, potassium methoxide, potassium ethoxide and potassium butoxide; and alkaline earth metal alkoxides such as calcium methoxide, calcium ethoxide, calcium butoxide, magnesium methoxide, magnesium ethoxide and magnesium butoxide. These may be used singly or two or more of them may be used combinedly. The amount of the metal hydroxides and/or metal alkoxides to be used in modifying the above metal oxide catalysts or composite metal oxide catalysts is preferred within the range of 0.1 to 20% by weight, more preferred within the range of 0.5 to 10% by weight, particularly preferred within the range of 1 to 5% by weight, based on the metal oxide catalysts or composite metal oxide catalysts. The above amount range for the metal hydroxides and/or metal alkoxides to be used in modifying the metal oxide catalysts or composite metal oxide catalysts is preferred in view of the yield, productivity and economy.

In the practice of the invention, the above reaction step is not particularly restricted but can be carried out according to the reaction type conventional in the art in carrying out this sort of reaction, for example in batch type, semibatch type or continuous type. When the reaction is conducted in batch type, for instance, the reaction is allowed to proceed by introducing the heterocyclic compounds into the α,β-unsaturated carboxylic acid esters or α,β-unsaturated carboxylic acids. It is also possible to dissolve the α,β-unsaturated carboxylic acid esters or α,β-unsaturated carboxylic acids in solvents and then introduce the heterocyclic compounds thereinto. When the reaction is carried out in continuous type, the α,β-unsaturated carboxylic acid esters or α,β-unsaturated carboxylic acids and the heterocyclic compounds are continuously fed to a tubular or tank reactor, for instance, and the reaction mixture is continuously discharged from the reactor. When the reaction is carried out in the presence of catalysts, the catalysts may be continuously fed to the reactor together with the starting materials and continuously discharged together with the reaction mixtures or, in the case of a tubular reactor, solid catalysts may be used in the so-called fixed bed form, namely packed in the reactor. In the case of a tank reactor, the solid catalysts may be used in the so-called fluidized bed form, namely fluidized together with the reaction mixture within the reactor.

The above catalysts may be in the form of a powder or moldings according to the mode of reaction, e.g. batch type, semibatch type or continuous type. For molding, it may be mixed with silica, alumina, silica-alumina or the like.

The amount of the catalysts to be used may vary depending on the combination of the α,β-unsaturated carboxylic acid esters of the general formula (1) with the heterocyclic compounds of the general formula (2) or the combination of the α,β-unsaturated carboxylic acids of the general formula (4) with the heterocyclic compounds of the general formula (5) but, it is preferred within the range of 0.001 to 25% by weight, more preferred within the range of 0.005 to 20% by weight, still more preferred within the range of 0.01 to 15% by weight, particularly preferred within the range of 0.05 to 10% by weight, based on the α,β-unsaturated carboxylic acid esters or α,β-unsaturated carboxylic acids. The above range of the catalysts amount is preferred for yield, productivity and economy reasons.

After completion of the reaction, the above catalysts can be easily separated from the reaction system by filtration or decantation and the catalysts so separated may be used again in the reaction according to the invention.

The polymerization inhibitors to be used in the practice of the invention are not particularly restricted but include the compounds in the following;

quinone type polymerization inhibitors such as hydroquinone, methoxyhydroquinone, benzoquinone and p-tert-butylcatechol, chloranil, 2-tert-butylhydroquinone, 2, 5-di-tert-butylhydroquinone, 2-tert-butylmethoxyhydroquinone and 2, 5-di-tert-aminohydroquinone;

alkylphenol type polymerization inhibitors such as 2,6-di-tert-butylphenol, 2,4-di-tert-butylphenol, 2-tert-butyl-4,6-dimethylphenol, 2,6-di-tert-butyl-4-methylphenol, 2,6-di-tert-butyl-4-ethylphenol, 2,4,6-tri-tert-butylphenol, 2,6-tert-butyl-4-hydroxymethylphenol, 2,6-di-tert-butyl-2-dimethylamino-p-cresol, n-octadecyl-3-(3',5'-di-tert-butyl-4'-hydroxyphenyl)propionate, 2,4-bis(n-octylthio)-6-(4-hydroxy-3,5-di-tert-butylanilino)-1,3,5-triazine, stylinate phenol, α-tocophenol, 2-tert-butyl-6-(3'-tert-butyl-5'-methyl-2'-hydroxybenzyl)-4-methylphenylacrylate, 2-[1-(2-hydroxy-3,5-di-tert-pentylphenyl)ethyl]-4,6-di-tert-pentylphenylacrylate, 2,2'-methylenebis(4-methyl-6-tert-butylphenol), 2,2'-methylenebis(4-ethyl-6-tert-butylphenol), 2,2'-methylenebis(6-cyclohexyl-4-methylphenol), 2,2'-methylenebis[6-(1-methylcyclohexyl)-p-cresol], 2,2'-ethylidenebis(2,4-di-tert-butylphenol), 2,2'-butylidenebis(2-tert-butyl-4-methylphenol), 4,4'-methylenebis(2,6-di-tert-butylphenol), 4,4'-butylidenebis(3-methyl-6-tert-butylphenol), 1,6-hexanediolbis[3-(3,5-di-tert-butyl-(4-hydroxyphenyl)]propionate, triethyleneglycolbis(3-tert-butyl-5-methyl-4-hydroxyphenyl) propionate, N,N'-bis[3-(3,5-di-tert-butyl-4-hydroxyphenyl) propionyl]hydrazine, N,N'-bis[3-(3',5'-di-tert-butyl-4-hydroxyphenyl) propionyl] hexamethylenediamine, 2,2-thiobis(4-methyl-6-tert-butylphenol), 4,4 -thiobis(3-methyl-6-tert-butylphenol), 2,2'-thiodiethylenebis[3-(3,5-di-tert-butyl-4-hydroxyphenyl ) propionate], bis[2-tert-butyl-4-methyl-6-(3-tert-butyl-5-methyl-4-hydroxybenzyl)phenyl]terephthalate, 1,1,3-tris(2-methyl-4-hydroxy-5-tert-butylphenyl)butane, 1,3,5-trimethyl-2,4,6-tris(3,5-di-tert-butyl-4-hydroxybenzy i)benzene, tris(3,5-di-tert-butyl-4-hydroxybenzyl)isocyanurate, tris[2-(3',5'-di-tert-butyl-4'-hydroxyhydro-cynamoyloxyl)et hyl] isocyanurate, tris(4-tert-butyl-2,6-di-methyl-3-hydroxybenzyl)isocyanurate, tetrakis[methylene-3-(3', 5'-di-tert-butyl-4'-hydroxyphenyl) propionate] methane, calcium-bis(ethyl-3,5-di-tert-butyl)-4-hydroxybenzylphosphate, propyl-3,4,5-trihydroxybenzenecarbonate, octyl-3,4,5-trihydroxybenzenecarbonate, dodecyl-3,4,5-trihydroxybenzenecarbonate, 2,2'-methylenebis(4-methyl-6-tert-butylphenol), 4,4-methylenebis(2,6-di-tertbutylphenol), 1,1-bis(4-hydroxyphenyl)cyclohexane, 1,1,3-tris(2-methyl-4-hydroxy-5-tert-butylphenyl) butane, 1,3,5-trimethyl-2,4,6-tris(3,5-di-tert-butyl-4-hydroxybenzy 1)benzene and 3,9-bis[1,1-dimethyl-2-{β-(3-tert-butyl-4-hydroxy-5-methylphenyl) propionyloxy}ethyl]-2,4,8,10-tetraoxaspiro[5,5] undecane;

amine type polymerization inhibitors such as alkylated diphenylamines, N,N'-diphenyl-p-phenylenediamine, 6-ethoxy-2,2,4-trimethyl-1,2-dihydroquinoline, N-phenyl-N'-isopropyl-p-phenylenediamine, N-phenyl-1,3-dimethylbutyl-p-phenylenediamine, 2,2,4-trimethyl-1,2-hydroquinoline polymer, aldol-α-naphtylamine, N-phenyl-β-naphtylamine, N,N'-di-2-naphtyl-p-phenylenediamine, 4,4'-dioctyldiphenylamine and phenothiazine;

copper dithiocarbamate type polymerization inhibitors such as copper dimethyldithiocarbamate, copper diethyldithiocarbamate, copper dipropyldithiocarbamate, copper dibutyldithiocarbamate, copper ethylenedithiocarbamate, copper tetramethylenedithiocarbamate, copper pentamethylenedithiocarbamate, copper hexamethylenedithiocarbamate, copper oxydiethylenedithiocarbamate;

piperidine type polymerization inhibitors such as 4-hydroxy-2,2,6,6-tetramethylpiperidine, 4-benzoyloxy-2,2,6,6-tetramethylpiperidine, 1,4-dihydroxy-2,2,6,6-tetramethylpiperidine and 1-hydroxy-4-benzoyloxy-2,2,6,6-tetramethylpiperidine;

N-oxyl type polymerization inhibitors such as 2,2,6,6-tetramethylpiperidine-N-oxyl, 4-hydroxy-2,2,6,6-tetramethylpiperidine-N-oxyl and 4-benzoyloxy-2,2,6,6-tetramethylpiperidine-N-oxyl;

sulfide type polymerization inhibitors such as sulfuric acid, dilauryl-3,3'-thiodipropionate, ditridecyl-3,3'-thiodipropionate, dimyristyl-3,3'-thiodipropionate, istearyl-3,3'-thiodipropionate, tetrakis-methylene-3-(laurylthio)propionate methane, distearyl-3,3'-methyl-3,3'-thiodipropionate, laurylstearyl-3,3'-thiodipropionate, bis[2-methyl-4-(3-n-alkylthiopropionyloxy)-5-tert-butylphen yl]sulfide, β-laurylthiopropionate, 2-mercaptobenzoimidazol and 2-mercapto-5-methylbenzoimidazol;

phosphorus type polymerization inhibitors such as tris (isodecyl)phosphite, tris(tridecyl)phosphite, phenyldiisooctylphosphite, phenyldiisodecylphosphite, phenyl di(tridecyl)phosphite, diphenyl isooctylphosphite, diphenylisodecylphosphite, diphenyltridecylphosphite, [1,1-diphenyl-4,4'-diylbistetrakis-2,4-bis-(1,1-dimethyleth yl)phenyl] phosphonate ester , triphenylphosphite, tris (nonylphenyl) phosphite, 4,4'-isopropyridenediphenol alkyl phosphite, tris(2,4-di-tert-butylphenyl)phosphite, tris(biphenyl)phosphite, distearylpentaerythritoldiphosphite, di(2,4-di-tert-butylphenyl)pentaerythritoldiphosphite, di(nonylphenyl) pentaerythritoldiphosphite, phenyl-bisphenol A pentaerythritoldiphosphite, tetra(tridecyl)-4,4'-butylidenebis(3-methyl-6-tert-butylphnol) diphosphite, hexa(tridecyl)-1,1,3-tris(2-methyl-4-hydroxy-5-tert-butylph enyl)butanetriphosphite, diethyl 3,5-di-tert-butyl-4-hydroxybenzylphosphate ester, sodium-bis(4-tert-butylphenyl)phosphate, sodium-2,2'-methylene-bis(4,6-di-tert-butylphenyl) phosphate, 1,3-bis(diphenoxyphosphonyloxy)benzene;

and N-nitrosophenylhydroxyamine type polymerization inhibitors such as aluminum N-nitrosophenylhydroxyamine, copper N-nitrosophenylhydroxyamine, ferric N-nitrosophenylhydroxyamine, tin N-nitrosophenylhydroxyamine, zinc N-nitrosophenylhydroxyamine, magnesium N-nitrosophenylhydroxyamine.

These may be used singly or two or more of them may be used combinedly.

Among these, judiciously used are hydroquinone, methoxyhydroquinone, benzoquinone, p-tert-butylcatechol, phenothiazine, 4-hydroxy-2,2,6,6-tetramethylpiperidine, 4-benzoyloxy-2,2,6,6-tetramethylpiperidine, 1,4-dihydroxy-2,2,6,6-tetramethylpiperidine, 1-hydroxy-4-benzoyloxy-2,2,6,6-tetramethylpiperidine, 2,2,6,6-tetramethylpiperidine-N-oxyl, 4-hydroxy-2,2,6,6-tetramethylpiperidine-N-oxyl and 4-benzoyloxy-2,2,6,6-tetramethylpiperidine-N-oxyl.

The addition amount of the polymerization inhibitors may vary depending on the species of the α,β-unsaturated carboxylic acid esters of the general formula (1) or of the α,β-unsaturated carboxylic acid of the general formula (4) but generally is within the range of 0.001 to 5% by weight, preferably 0.005 to 1% by weight, more preferably 0.01 to 0.1% by weight, based on said α,β-unsaturated carboxylic acid esters or α,β-unsaturated carboxylic acids. The above addition amount range for the polymerization inhibitors is preferred from the viewpoints of polymerization inhibition, yield, productivity and economy.

The reaction temperature for the reaction of the α,β-unsaturated carboxylic acid esters of the general formula (1) with the heterocyclic compounds of the general formula (2) is not particularly restricted but is preferred within the range of 0° C. to 230° C., more preferred within the range of 30° C. to 200° C., particularly preferred within the rang eof 50° C. to 180° C. The reaction temperature for the reaction of the α,β-unsaturated carboxylic acids of the general formula (4) with the heterocyclic compounds of the general formula (5) is not particularly restricted but is preferred within the range of 0° C. to 230° C., more preferred within the range of 20° C. to 200° C., particularly preferred within the range of 30° C. to 180° C. The reaction pressure is not particularly restricted but the reaction may be carried out at ordinary pressure (atmospheric pressure) or under pressurization. The reaction time may appropriately be selected according to the species of the α,β-unsaturated carboxylic acid esters or α,β-unsaturated carboxylic acids, of the heterocyclic compounds, of the catalysts and of the organic solvents or combination of these and the amounts thereof so that the above reaction may be driven to completion.

In the practice of the invention, the particular use of solvents is not necessary but organic solvents maybe used. The organic solvents are not particularly restricted but include, among others, aromatic hydrocarbons such as benzene, toluene and xylene; aliphatic hydrocarbons such as pentane, hexane, cyclohexane and heptane; ethers such as diethyl ether and diisopropyl ether; and halogenated hydrocarbons such as chloroform, methylene chloride, dichloroethane and chlorobenzene. These may be used singly or two or more of them may be used combinedly.

The required amount of the organic solvents may vary according to the combination of the α,β-unsaturated carboxylic acid esters of the general formula (1) with the heterocyclic compounds of the general formula (2) or of the combination of the α,β-unsaturated carboxylic acids of the general formula (4) with the heterocyclic compounds of the general formula (5) but generally within the range of Oto 200% by weight, preferably 0 to 100% by weight, more preferably 0 to 80% by weight, particularly preferably 0 to 70% by weight, based on the total amount of the α,β-unsaturated carboxylic acid esters of the general formula (1) and the heterocyclic compounds of the general formula (2) or of the α,β-unsaturated carboxylic acids of the general formula (4) and the heterocyclic compounds of the general formula (5). The above amount range for the organic solvents is preferred from the viewpoints of yield, productivity and economy.

When, in the practice of the invention, the starting material heterocyclic compounds are alkylene oxides, the reaction in the above reaction step is preferably carried out in an oxygen-free atmosphere. If the reaction is carried out in an oxygen-containing atmosphere, the alkylene oxides may form an explosive mixed gas under certain conditions in the presence of oxygen, causing the safety of the reaction to decrease. On the other hand, in an atmosphere absolutely free of oxygen, the starting materials and products may polymerize due to free of oxygen. It is therefore preferable to carry out the reaction in a gaseous atmosphere containing oxygen as a polymerization inhibitor. However, when the production reaction is carried out in a mixed gas atmosphere containing a relatively high concentration of oxygen, for example under air, the possibility of an explosive mixed gas being formed on the occasion of charging the alkylene oxides into the reactor is especially high, incurring a great danger.

Even when, in the above reaction step using alkylene oxides as starting materials, the reaction is carried out in a mixed gas atmosphere containing oxygen at a relatively low concentration, inert gases such as nitrogen, which is a sealing gas (sealing gas for pressurization or purging for the tanks in which the raw materials are stored) and oxygen are dissolved and contained in the starting materials α,β-unsaturated carboxylic acid esters or α,β-unsaturated carboxylic acids and the alkylene oxides, and therefore the concentration of oxygen in the gaseous phase in the reactor changes upon each charging of these raw materials and, as the oxygen concentration becomes increased, the danger of explosion increases while, as the oxygen concentration approaches 0% by volume, the possibility of polymerization arises due to free of oxygen. During progress of the reaction, too, the concentration of oxygen in the gaseous phase in the reactor may change in certain instances. Therefore, in producing the desired α,β-unsaturated carboxylic acid esters by reacting the α,β-unsaturated carboxylic acid esters or α,β-unsaturated carboxylic acids with the alkylene oxides, the oxygen amount in the gaseous phase in the reactor is preferably maintained within a specific low concentration range at every stage, before and after charging the raw materials, during reaction and after reaction. In discussing the oxygen concentration, the volume of the whole gaseous phase in the reactor is taken as 100% by volume.

In the above reaction step, it is preferred that (1) the oxygen concentration in gaseous phase in the reactor before alkylene oxides charging be maintained at 0.1 to 8% by volume by using an oxygen/inert gas mixture adjusted beforehand to an oxygen concentration of 0.1 to 8% by volume and/or an inert gas, (2) the concentration of oxygen in the gaseous phase in the reactor during reaction is maintained at 0.1 to 8% by volume by using an oxygen/inert gas mixture adjusted beforehand to an oxygen concentration of 0.1 to 8% by volume and/or an inert gas and (3) the concentration of oxygen in the gaseous phase in the reactor after completion of the reaction until the next charging for the next reaction run is maintained at 0.1 to 8% by volume by using an oxygen/inert gas mixture adjusted beforehand to an oxygen concentration of 0.1 to 8% by volume and/or an inert gas. Thus, at each stage, namely before reaction, during reaction and after reaction until the next charging for the next reaction run, the oxygen concentration of the gaseous phase in the reactor is preferably maintained at 0.1 to 8% by volume. By this, the formation of an explosive mixed gas can be prevented and the polymerization due to free of oxygen can also be inhibited. A preferred range is 0.3 to 7.5% by volume and a more preferred range is 0.5 to 7.0% by volume.

In the above reaction step, prior to alkylene oxides charging, for instance, the starting materials α,β-unsaturated carboxylic acid esters or α,β-unsaturated carboxylic acids are charged into the reactor in advance. Since the sealing gas mentioned above has been dissolved in the α,β-unsaturated carboxylic acid esters or α,β-unsaturated carboxylic acids, the oxygen concentration of the gaseous phase in the reactor may change as a result of charging of the α,β-unsaturated carboxylic acid esters or α,β-unsaturated carboxylic acids even when the oxygen concentration in the gaseous phase space in the reactor has been adjusted to a level within the range mentioned above before charging the α,β-unsaturated carboxylic acid esters or α,β-unsaturated carboxylic acids. Therefore, according to such change, the oxygen concentration is adjusted by adding an oxygen/inert gas mixture adjusted beforehand to an oxygen concentration of 0.1 to 8% by volume and/or an inert gas to the gaseous phase space in the reactor. According to a specific method of oxygen concentration adjustment, when the oxygen concentration of the gaseous phase in the reactor increases, for instance, the oxygen concentration is decreased by adding an inert gas. When, conversely, the oxygen amount in the gaseous phase in the reactor declines, the oxygen concentration is increased by adding an oxygen/inert gas mixture adjusted beforehand to an oxygen concentration of 0.1 to 8% by volume. In this manner, the oxygen concentration of the gaseous phase in the reactor is maintained within the range of 0.1 to 8% by volume. If, in adjusting the oxygen concentration, an inert gas has been added in excess, for instance, the concentration of oxygen in the gaseous phase in the reactor may be again adjusted by adding an oxygen/inert gas mixture adjusted beforehand to an oxygen concentration of 0.1 to 8% by volume, as the case may be.

Further, in the above reaction step, after alkylene oxides charging and during reaction, the oxygen concentration of the gaseous phase in the reactor may change as a result of alkylene oxides charging since the alkylene oxides contain the above-mentioned sealing gas dissolved therein, like in the case mentioned above. Therefore, according such change, the oxygen concentration is adjusted by adding an oxygen/inert gas mixture adjusted beforehand to an oxygen concentration of 0.1 to 8% by volume and/or an inert gas to the gaseous plenum in the reactor. The specific method of oxygen concentration adjustment is the same as mentioned above.

In cases where the above reaction step is carried out in a continuous manner, it is also useful to maintain the oxygen concentration within the range of 0.1 to 8% by volume, since the oxygen concentration of the gaseous phase in the reactor may change, for example under the influence of the sealing gas dissolved in the α,β-unsaturated carboxylic acid esters or α, β-unsaturated carboxylic acids and in the alkylene oxides, which are fed continuously to the reactor.

After completion of the reaction, the reaction mixture is discharged from the reactor, whereupon the reactor inside pressure is reduced. It is then necessary to compensate for the internal pressure reduction by introducing a gas under pressure from the outside. In some cases, the reaction mixture is discharged from the reactor by introducing a gas under pressure from the outside from the beginning. By these procedures, the oxygen concentration of the gaseous phase in the reactor may be altered. If the oxygen concentration of the gas introduced under pressure from the outside is high, an explosive gas mixture may be formed when the alkylene oxides remain in the reactor. This is very dangerous. Therefore, an oxygen/inert gas mixture adjusted beforehand to an oxygen concentration of 0.1 to 8% by volume and/or an inert gas are/is used as the gas in performing the above procedures and the oxygen concentration of the gaseous phase in the reactor is maintained within the range of 0.1 to 8% by volume. Further, if, by using an oxygen/inert gas mixture adjusted beforehand to an oxygen concentration of 0.1 to 8% by volume and/or an inert gas, the oxygen concentration of the gaseous phase in the reactor is adjusted and maintained within the range of 0.1 to 8% by volume even after reaction mixture discharging until the next charging, the possibility of an explosive mixed gas being formed from the alkylene oxides remaining in the reactor will be reduced and an effect will be produced in maintaining the reactor in a safe condition without allowing polymerization of the residual reaction mixtures within the reactor (valve, nozzle site, etc.).

According to a concrete method of controlling the oxygen concentration in the gaseous phase space in the reactor in the above reaction step, the oxygen/inert gas mixture and/or inert gas may be introduced continuously or intermittently, and these gases may be introduced into the gaseous plenum in the reactor or bubbled into the reaction mixture. In each case, a dispersing plate may be disposed for improving the dispersion of gas (es). The reactor inside pressure is increased by the introduction of these gases, as the case may be. In that case, the gas (es) may be purged intermittently or, when the gas(es) is(are) introduced continuously, the gas (es) maybe purged continuously.

The reactor inside pressure in the above reaction step is preferably within the range of 0.05 to 3 MPa, more preferably within the range of 0.1 to 2 Mpa, and still more preferably within the range of 0.1 to 1 Mpa. If the reactor inside pressure is lower than 0.05 MPa, the alkylene oxide cannot occur as a liquid under reaction temperature conditions and the progress of the reaction will become slow. At above 3 MPa, a reactor higher in pressure resistance is required and this is economically unfavorable. The alkylene oxides contained in the gas purged from the reactor, inclusive of the purging gas, may be caused to be absorbed in water and then discarded. It is economically preferable, however, to recover the same for reuse by introducing the gas discharged into alkylene oxides recovery plant and causing the same to be condensed in a condenser for recovering the same or causing the same to be absorbed in polar solvents such as water or the starting material α,β-unsaturated carboxylic acid esters or α,β-unsaturated carboxylic acids or the product α,β-unsaturated carboxylic acid esters for reuse thereof. In particular, it is preferable to recover and reuse the alkylene oxides by causing the same to be absorbed in the starting material α,β-unsaturated carboxylic acid esters or α,β-unsaturated carboxylic acids or the product α,β-unsaturated carboxylic acid esters or mixtures thereof.

In reacting the above α,β-unsaturated carboxylic acid esters or α,β-unsaturated carboxylic acids with alkylene oxides to thereby produce the corresponding α,β-unsaturated carooxylic acid esters, it may be said to be a preferred mode of practice to maintain the oxygen concentration in the gaseous phase space in the reactor at 0.1 to 8% by volume throughout the production process. This is because, if such a low oxygen concentration can be maintained throughout the production process, safe and stable production can be realized. Generally, the above production process comprises the reaction steps, the step of separating the unreacted alkylene oxides, the step of separating the unreacted α,β-unsaturated carboxylic acid esters or the unreacted α,β-unsaturated carboxylic acids and the step of distilling the products. When the conversion of the α,β-unsaturated carboxylic acid esters or α,β-unsaturated carboxylic acids in the reaction step is nearly 100%, the step of separating the unreacted α,β-unsaturated carboxylic acid esters or unreacted α,β-unsaturated carboxylic acids may be omitted.

The step of separating the unreacted alkylene oxides comprises, for example, separating or removing the unreacted alkylene oxides from the postreaction mixture by means of an inert gas using a packed column, and causing the alkylene oxides in that gas to be absorbed in solvents such as water, followed by discarding or recovery for reuse.

The step of separating the unreacted α,β-unsaturated carboxylic acid esters or unreacted α,β-unsaturated carboxylic acids comprises, for example, separating or removing the unreacted α,β-unsaturated carboxylic acid esters or unreacted α,β-unsaturated carboxylic acids from the post reaction mixture by distillation using a distillation still and causing the vapor (distillate) to condense in a condenser or to be absorbed in solvents such as water, followed by discarding or recovery for reuse. The step of distilling the products comprises, for example, distilling the products using a distillation still and causing the same to condense in a condenser or the like to thereby obtain the products.

When alkylene oxides are used as a raw material, a more preferred mode of practice of the invention comprises maintaining the oxygen concentration at 0.1 to 8% by volume not only in the gaseous phase in the reactor but also in the gaseous phase spaces in the step of separating the unreacted alkylene oxides from the product, namely in the gaseous phase spaces in the packed column, in the gaseous phase spaces in the vapor line and so on until absorption of the gas derived from the packed column in a solvent such as water and in the gaseous phase spaces in intermediate tanks such as the feed tank belonging to the packed column in the above example.

Within the scope of the above mode of practice, a more preferred mode of practice comprises maintaining the oxygen concentration at 0.1 to 8% by volume also in the gaseous phase spaces in the step of separating the unreacted α,β-unsaturated carboxylic acid esters or unreacted α,β-unsaturated carboxylic acids from the product, namely in the gaseous phase spaces in the distillation still, in the gaseous phase spaces in the vapor line and so on until condensation of the vapor derived from the distillation still in a condenser or the like or absorption thereof in solvents such as water and in the gaseous phase spaces in intermediate tanks such as the feed tank and distillate tank belonging to the distillation still in the above example and/or in the gaseous phase spaces in the step of distilling the products, namely in the gaseous phase spaces in the distillation still, in the gaseous phase spaces in the vapor line and so on until condensation of the vapor derived from the distillation still in a condenser or the like and in the gaseous phase spaces in intermediate tanks such as the feed tank and distillate tank belonging to the distillation still in the above example.

The apparatuses to be used in the above step of separating the unreacted alkylene oxides, unreacted α,β-unsaturated carboxylic acid esters or unreacted α,β-unsaturated carboxylic acids and in the step of distilling the product are not particularly restricted but include packed columns, plate columns, bubble-cap plate columns and distillation stills, among others.

By maintaining the oxygen concentration in other gaseous phase spaces than that in the reactor at 0.1 to 8% by volume in the step of separating the unreacted alkylene oxides from the product, it becomes possible to reduce the possibility of an explosive mixed gas being formed from the gas in such gaseous phase spaces and the alkylene oxides and thus safely produce the α,β-unsaturated carboxylic acid esters without allowing polymer formation in the step of separating the unreacted raw materials or in the step of distilling the products. If a gas having a high oxygen concentration, for example air, is used as the oxygen source in lieu of an oxygen/inert gas mixture adjusted beforehand to an oxygen concentration of 0.1 to 8% by volume and/or an inert gas, the possibility of an explosive gas high in oxygen concentration being formed locally, for example in the vicinity of the air introduction nozzle will become high even when the oxygen concentration in the whole gaseous phase space in the reactor is within the range of 0.1 to 8% by volume.

The α,β-unsaturated carboxylic acid heterocycle-inserted esters or α,β-unsaturated carboxylic acid polyheteroalkylene esters in the practice of the invention can be recovered after the above reaction process, if necessary by conducting the step of purification of the solution obtained separately from or in addition to the steps mentioned above. The means of purification is not particularly restricted but the separation/purification purposes can be accomplished, for example, by distillation, extraction and column chromatography. These means may be employed singly or in combination.

The present invention further provides a catalyst for the production of α,βunsaturated carboxylic acid esters of the general formula (7):

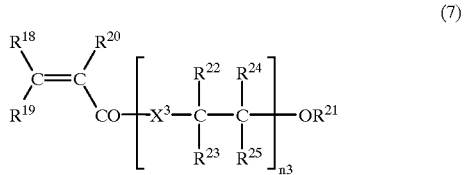

(7)

wherein $R^{18}$, $R^{19}$ and $R^{20}$ are the same or different and each represents a hydrogen atom or an organic residue, $R^{21}$ represents a hydrogen atom or an organic residue, one of $R^{22}$, $R^{23}$, $R^{24}$ and $R^{25}$ represents an organic residue and the remaining three each represents a hydrogen atom, $X^3$ represents O, S or NH and n3 represents an positive integer not less than 1, which catalyst comprises a metal oxide.

The above catalysts preferably comprise metal oxides as a main component thereof and may contain another component or other components additionally.

Referring to the above general formula (7), the organic residue represented by $R^{18}$, $R^{19}$ or $R^{20}$ is not particularly restricted but includes, among others, those mentioned hereinabove referring to $R^1$, $R^2$ or $R^3$. The organic residue represented by $R^{21}$ is not particularly restricted but includes, among others, those mentioned hereinabove referring to $R^4$. The organic residue constituting one of $R^{22}$, $R^{23}$, $R^{24}$ and $R^{25}$ is not particularly restricted but includes, among others, those mentioned hereinabove referring to $R^5$.

The above metal oxides are not particularly restricted but includes, among others, those metal oxides specifically mentioned hereinabove. As a preferred mode of embodiment, there may be mentioned (1) the use, as the metal oxides, of one of the composite metal oxides mentioned hereinabove and (2) the use, as the metal oxides, of such metal oxides surface-modified with metal hydroxides and/or metal alkoxides as mentioned hereinabove, among others.

The catalysts of the invention which comprise metal oxides can be used in the production of the α,β-unsaturated carboxylic acid esters represented by the above general formula (7). In particular, it is judiciously used in the process for producing α,β-unsaturated carboxylic acid esters which comprises the step of reacting α,β-unsaturated carboxylic acid esters of the general formula (1) with heterocyclic compounds of the general formula (2) to give α,β-unsaturated carboxylic acid esters of the general formula (3) or in the process for producing α, β-unsaturated carboxylic acid esters which comprises the step of reacting α,β-unsaturated carboxylic acids of the general formula (4) with heterocyclic compounds of the general formula (5) in the presence of polymerization inhibitors to give α, β-unsaturated carboxylic acid esters of the general formula (6), and they are catalysts suited for use in the production of a, 1 -unsaturated carboxylic acid esters in an economical and efficient manner.

According to the process of the invention, α,β-unsaturated carboxylic acid heterocycle-inserted esters of the general formula (3) can be produced economically and with good productivity and α,β-unsaturated carboxylic acid polyheteroalkylene esters of the general formula (6) containing a almost no α,β-unsaturated carboxylic acid diesters can be produced economically and with good productivity, with the distribution of numbers of moles of the heterocyclic compounds added being sharp.

When the catalysts of the invention are used, the α, β-unsaturated carboxylic acid heterocycle-inserted esters of the general formula (3) or α,β-unsaturated carboxylic acid polyheteroalkylene esters of the general formula (6) can be produced economically and with good productivity.

The α,β-unsaturated carboxylic acid heterocycle-inserted esters of the general formula (3) and α, β-unsaturated carboxylic acid polyheteroalkylene esters of the general formula (6) can be used in a wide range of application, for example as raw materials for the production of perfumes, medicinals and agrochemicals, as intermediates in organic synthesis and as polymerizable materials.

EXAMPLES

The following examples illustrate the invention in further detail. They are, however, by no means limitative of the scope of the invention.

Example 1

Production of Catalyst A

A commercial magnesium oxide powder (25 g; product of Kyowa Kagaku Kogyo; Kyowamag 150) was calcined at 600° C. in a nitrogen atmosphere for 3 hours to give 22 g of a magnesium oxide catalyst.

Example 2

Production of Catalyst B

A commercial aluminum-magnesium hydroxide powder (50 g; product of Kyowa Kagaku Kogyo; Kyowaad 300) was calcined at 700° C. in a nitrogen atmosphere for 3 hours to give 28 g of a Mg-Al-based composite metal oxide catalyst.

Example 3

Production of Catalyst C

The Mg—Al-based mixed oxide (10 g) obtained in Example 2 was placed in a 300-ml beaker, 200 ml of ethanol was added, and the mixture was stirred. With stirring at room temperature, 14.25 ml of 0.5 N ethanolic potassium hydroxide was added, and the stirring was continued for further 2 hours. Thereafter, the mixture was filtered and the solid was washed with ethanol and then dried at 50° C. under reduced pressure to give 10.4 g of an Mg-Al-based composite metal oxide catalyst surface-modified with potassium hydroxide.

Example 4

A 100-ml autoclave made of Hastelloy C and equipped with a thermometer, a stirrer, a pressure gauge and an inlet tube was charged with 17.2 g of methyl acrylate, 17 mg of phenothiazine and 0.5 g of catalyst A and then the autoclave was completely purged with 2.5% by volume of oxygen (the balance being nitrogen) To this reaction system was added 8.8 g of ethylene oxide. The contents were gradually heated with stirring and the inside temperature was raised to 150° C.

Then, the reaction was driven to completion by stirring at 150° C. for 5 hours. After completion of the reaction, the catalyst was filtered off from the reaction mixture and the filtrate obtained was analyzed using a model GC-1700 gas chromatograph (product of Shimadzu Corp.; hereinafter referred to as "GC"). The whole amount of ethylene oxide was found to have reacted to give 0.10 mole of the adduct containing 1 mole of EO, 0.03 mole of the adduct containing 2 moles of EO, 0.01 mole of the adduct containing 3 moles of EO and 0.003 mole of the adduct containing 4 moles of EO.

Example 5

The same procedure as in Example 4 was followed except that 0.5 g of catalyst B was used as the catalyst. Analysis using the GC showed that the whole amount of ethylene oxide had reacted to give 0.13 mole of the adduct containing 1 mole of EO, 0.02 mole of the adduct containing 2 moles of EQ and 0.01 mole of the adduct containing 3 moles of EO.

Example 6

The same procedure as in Example 4 was followed except that 0.5 g of catalyst C was used as the catalyst. Analysis using the GC showed that the whole amount of ethylene oxide had reacted to give 0.15 mole of the adduct containing 1 mole of EO, 0.02 mole of the adduct containing 2 moles of EO and 0.03 mole of the adduct containing 3 moles of EO.

Example 7

The same procedure as in Example 4 was followed except that 0.5 g of catalyst C was used as the catalyst and ethylene oxide was used in an amount of 17.6 g. Analysis using the GC showed that the whole amount of ethylene oxide had reacted to give 0.05 mole of the adduct containing 1 mole of EO, 0.11 mole of the adduct containing 2 moles of EO, 0.02 mole of the adduct containing 3 moles of EO and 0.017 mole of the adduct containing 4 moles of EO.

Example 8

The same procedure as in Example 4 was followed except that 0.5 g of catalyst C was used as the catalyst and 20.0 g of ethyl acrylate was used in lieu of methyl acrylate. Analysis using the GC showed that the whole amount of ethylene oxide had reacted to give 0.15 mole of the adduct containing 1 mole of EO, 0.02 mole of the adduct containing 2 moles of E. and 0.003 mole of the adduct containing 3 moles of EO.

Example 9

The same procedure as in Example 4 was followed except that 0.5 g of catalyst C was used as the catalyst and 20.0 g of methyl methacrylate was used in lieu of methyl acrylate. Analysis using the GC showed that the whole amount of ethylene oxide had reacted to give 0.15 mole of the adduct containing 1 mole of EG, 0.02 mole of the adduct containing 2 moles of EO and 0.003 mole of the adduct containing 3 moles of EO.

Example 10

The same procedure as in Example 4 was followed except that 0.5 g of catalyst C was used as the catalyst and 19.6 g of vinyl acrylate was used in lieu of methyl acrylate. Analysis using the GC showed that the whole amount of ethylene oxide had reacted to give 0.15 mole of the adduct containing 1 mole of EO, 0.02 mole of the adduct containing 2 moles of EO and 0.003 mole of the adduct containing 3 moles of EO.

Example 11

The same procedure as in Example 4 was followed except that 11.6 g of propylene oxide was used in lieu of ethylene oxide. Analysis using the GC showed that the whole amount of propylene oxide had reacted to give 0.10 mole of the adduct containing 1 mole of PO, 0.03 mole of the adduct containing 2 moles of P0, 0.01 mole of the adduct containing 3 moles of PO and 0.003 mole of the adduct containing 4 moles of PO.

Example 12

The same apparatus as used in Example 4 was charged with 21.6 g of acrylic acid, 11 mg of phenothiazine, 20.9 g of propylene oxide and 1.0 g of catalyst A. The autoclave inside was then completely purged with 2.5% by volume of oxygen (the balance being nitrogen). The contents were slowly heated with stirring and the reaction was driven to completion by stirring at an inside temperature of 70° C. for 4 hours. After completion of the reaction, the catalyst was removed by filtration and the filtrate obtained was analyzed using the GC. It was found that the conversion of acrylic acidwas 55.8 mole percent, the selectivity for the adduct containing 1 mole of propylene oxide (PO) was 80.3 mole percent, that for the adduct containing 2 moles of PO was 18.2 mole percent and that for the adducts containing 3 moles or more of PO was 1.1 mole percent. The selectivity toward the byproduct diester was 0.4 mole percent.

Example 13

The same procedure as in Example 12 was followed except that 1.0 g of catalyst B was used as the catalyst. Analysis using the GC revealed that the conversion of acrylic acid was 68.1 mole percent, the selectivity for the adduct containing 1 mole of propylene oxide was 86.2 mole percent, that for the adduct containing 2 moles of PO was 13.2 mole percent and that for the adducts containing 3 moles or more of PO was 0.5 mole percent. The selectivity toward the byproduct diester was 0.1 mole percent.

Example 14

The same procedure as in Example 12 was followed except that 1.0 g of catalyst C was used as the catalyst. Analysis using the GC revealed that the conversion of acrylic acid was 65.6 mole percent, the selectivity for the adduct containing 1 mole of propylene oxide was 85.8 mole percent, that for the adduct containing 2 moles of PO was 13.6 mole percent and that for the adducts containing 3 moles or more of PO was 0.5 mole percent. The selectivity toward the byproduct diester was 0-1 mole percent.

Example 15

The same apparatus as used in Example 4 was charged with 21.6 g of acrylic acid, 11 mg of phenothiazine and 1.0 g of catalyst B. The autoclave inside was then completely purged with 2.5% by volume of oxygen (the balance being nitrogen). Then, 15.8 g of ethylene oxide was added and the contents were heated gradually and the reaction was driven to completion by stirring at an inside temperature of 70° C. for 4 hours.

After completion of the reaction, the reaction mixture was analyzed using the GC, which showed that the conversion of acrylic acid was 90.2 mole percent, the selectivity for the adduct containing 1 mole of ethylene oxide was 94.2 mole percent, that for the adduct containing 2 moles of EO was 5.1 mole percent and that for the adducts containing 3 moles or more of EO was 0.5 mole percent. The selectivity toward the byproduct diester was 0.2 mole percent.

Comparative Example 1

The same procedure as in Example 4 was followed except that the autoclave inside was completely purged with nitrogen instead of 2.5% by volume of oxygen (the balance being nitrogen). As a result, white polymer appeared so that even stirring became difficult after 2 hours.

Comparative Example 2

The same procedure as in Example 4 was followed except that the polymerization inhibitor phenothiazine was not added (the reaction system was free of polymerization inhibitor). As a result, white polymer appeared so that even stirring became difficult after 2 hours.

Comparative Example 3

The same procedure as in Example 12 was followed except that the autoclave inside was completely purged with nitrogen instead of 2.5% by volume of oxygen (the balance being nitrogen) As a result, white polymer appeared so that even stirring became difficult after 3 hours.

Comparative Example 4

The same procedure as in Example 12 was followed except that the polymerization inhibitor phenothiazine was not added (the reaction system was free of polymerization inhibitor). As a result, white polymer appeared so that even stirring became difficult after 2 hours.

What is claimed is:

1. A process for producing an α,β-unsaturated carboxylic acid ester which comprises the step of reacting an α,β-unsaturated carboxylic acid ester of general formula (1):

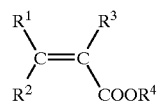

(1)

wherein $R^1$, $R^2$ and $R^3$ are the same or different and each represents a hydrogen atom or straight, branched or cyclic, satured and/or unsaturated alkyl group containing 1 to 20 carbon atoms, hydroxyalkyl group containing 1 to 10 carbon atoms, alkoxyalkyl group containing 1 to 10 carbon atoms, haloalkyl group containing 1 to 10 carbon atoms, acyloxy group containing 1 to 10 carbons atoms, acyloxy alkyl group containing 1 to 20 carbon atoms, aryl group, which may optionally have a substituent(s), a carboxyl group, carboxylic acid ester group represented by –COOR or amido group, R represents the same group as $R^4$ and $R^4$ represents straight, branched or cyclic, saturated and/or unsaturated alkyl group conataining 1 to 20 carbon atoms, hydroxyalkyl group containing 1 to 10 carbon atoms, alkoxyalkyl group containing 1 to 10 carbon atoms, haloalkyl group containing 1 to 10 carbon atoms, or aryl group, which may optionally have a substituent(s) with a heterocyclic compound of the general formula (2):

(2)

wherein $R^5$ represents a hydrogen atom or straight, branched or cyclic, saturated and/or alkyl group containing 1 to 10 carbon atoms, hydroxyalkyl group containing 1 to 5 carbon atoms, haloalkyl group containing 1 to 5 carbon atoms or aryl group and $X^1$ represents O, S or NH, in the presence of a polymerization inhibitor and a metal oxide catalyst to give an α,β-unsaturated carboxylic acid ester of the general formula (3):

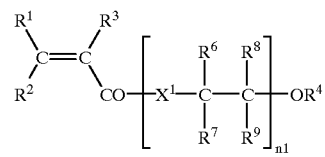

(3)

wherein $R^1$, $R^2$ and $R^3$ are the same or different as defined above, $R^4$ represents a group as defined above, one of $R^6$, $R^7$, $R^8$ and $R^9$ represents $R^5$ and the remaining three each represents a hydrogen atom, $X^1$ represents O, S or NH and n1 represents a positive integer not less than 1.

2. A process for producing an α,β-unsaturated carboxylic acid ester which comprises the step of reacting an α,β-unsaturated carboxylic acid of the general formula (4):

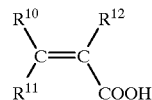

(4)

wherein $R^{10}$, $R^{11}$ and $R^{12}$ are the same or different and represents a hydrogen atom or, straight, branched or cyclic, saturated and/or unsaturated alkyl group containing 1 to 20 carbon atoms, hydroxyalkyl group containing 1 to 10 carbon atoms, alkoxyalkyl group containing 1 to 10 carbon atoms, haloalkyl group containing 1 to 10 carbon atoms, acyloxy group containing 1 to 10 carbon atoms, acyloxy alkyl group containing 1 to 20 carbon atoms, aryl group, which may optionally have a substituent(s), a carboxyl group, carboxylic acid ester represented by –COOR or amido group, R represents straight, branched or cyclic, saturated and/or unsaturated alkyl group containing 1 to 20 carbons, hydroxyalkyl group containing 1 to 10 carbons atoms, alkoxyalkyl group containing 1 to 10 carbon atoms, haloalkyl group containing 1 to 10 carbon atoms, or aryl group, which may optionally have a substituent(s), with a heterocyclic compound of the general formula (5):

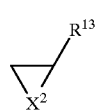

(5)

wherein $R^{13}$ represents a hydrogen atom or straight, branched or cyclic, saturated and/or unsaturated alkyl group containing 1 to 10 carbon atoms, hydroxyalkyl group containing 1 to 5 carbon atoms, haloakyl group containing 1 to 5 carbon atoms or aryl group.

and $X^2$ represents O, S or NH, in the presence of a polymerization inhibitor and a metal oxide catalyst to give an α,β-unsaturated carboxylic acid ester of the general formula (6):

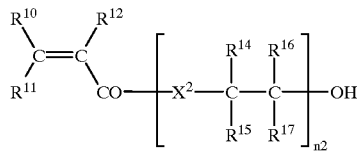

(6)

wherein $R^{10}$, $R^{11}$ and $R^{12}$ are the same or different as defined above, one of $R^{14}$, $R^{15}$, $R^{16}$ and $R^{17}$ represents $R^{13}$ and the remaining three each represents a hydrogen atom, $X^2$ represents O, S or NH and n2 represents a positive integer not less than 1.

3. The process of producing an α, β-unsaturated carboxylic acid ester according to claim 1,
wherein the metal oxide is a composite metal oxide.

4. The process for producing an α, β-unsaturated carboxylic acid ester according to claim 2,
wherein the metal oxide is a composite metal oxide.

5. The process for producing an α, β-unsaturated carboxylic acid ester according to claim 1,
wherein the metal oxide is metal oxide surface-modified with a metal hydroxide and/or a metal alkoxide.

6. The process for producing an α, β-unsaturated carboxylic acid ester according to claim 2,
wherein the metal oxide is metal oxide surface-modified with a metal hydroxide and/or a metal alkoxide.

7. The process for producing am α, β-unsaturated carboxylic acid ester according to claim 4,
wherein the metal oxide is metal oxide surface-modified with a metal hydroxide and/or a metal alkoxide.

8. The process for producing an α, β-unsaturated carboxylic acid ester according to claim 3, wherein the metal oxide is metal oxide surface-modified with a metal hydroxide and/or a metal alkoxide.

9. The process for producing an α, β-unsaturated carboxylic acid ester according to claim 1, wherein the reaction step is carried out at an oxygen concentration of 0.1 to 8% by volume in gaseous phase.

10. The process for producing an α, β-unsaturated carboxylic acid ester according to claim 2, wherein the reaction step is carried out at an oxygen concentration of 0.1 to 8% by volume in gaseous phase.

11. The process for producing an α, β-unsaturated carboxylic acid ester according to claim 3, wherein the reaction step is carried out at an oxygen concentration of 0.1 to 8% by volume in gaseous phase.

12. The process for producing an α, β-unsaturated acrboxylic acid ester according to claim 4, wherein the reaction step is carried out at an oxygen concentration of 0.1 to 8% by volume in gaseous phase.

13. The process for producing an α, β-unsaturated carboxylic acid ester according to claim 5, wherein the reaction step is carried out at an oxygen concentration of 0.1 to 8% by volume is gaseous phase.

14. The process for producing an α, β-unsaturated carboxylic acid ester according to claim 6, wherein the reaction step is carried out at an oxygen concentration of 0.1 to 8% by volume is gaseous phase.

15. The process for producing an α, β-unsaturated carboxylic acid ester according to claim 7, wherein the reaction step is carried out at an oxygen concentration of 0.1 to 8% by volume is gaseous phase.

16. The process for producing an α, β-unsaturated carboxylic acid ester according to claim 8, wherein the reaction step is carried out at an oxygen concentration of 0.1 to 8% by volume is gaseous phase.

17. The process for producing an α, β-unsaturated carboxylic acid ester according to claim 1, wherein the metal oxide catalyst is seperated from the reaction system by filteration or decantation after completion of reaction.

18. The process for producing an α, β-unsaturated carboxylic acid ester according to claim 2, wherein the metal oxide catalyst is seperated from the reaction system by filtration or decantation after completion of the reaction.

19. The process for producing an α, β-unsaturated carboxylic acid ester according to claim 1, wherein the metal oxide catalyst consists essentially of a metallic element and an oxygen element.

20. The process for producing an α, β-unsaturated carboxylix acid ester according to claim 2, wherein the metal oxide catalyst consists essentially of a metallic element and an oxygen element.

21. The process for producing an α, β-unsaturated carboxylic acid ester according to claim 1, wherein an ester product resulting from the reaction step consists essentially of the α, β-unsaturated carboxylic acid ester of the general formula (6 ).

22. The process for producing an α, β-unsaturated carboxylic acid ester according to claim 2, wherein an ester product resulting from the reaction step consists essentially of the α, β-unsaturated carboxylic acid ester of the general formula (6).

23. The process for producing an α, β-unsaturated carboxylic acid ester according to claim 1, wherein the reaction step is carried out without the polymerization of the α, β-unsaturated carboxylic acid ester.

24. The process for producing an α, β-unsaturated carboxylic acid ester according to claim 2, wherein the reaction step is carried out without the polymerization of the α, β-unsaturated carboxylic acid or the α, β-unsaturated carboxylic acid ester.

* * * * *

UNITED STATES PATENT AND TRADEMARK OFFICE
CERTIFICATE OF CORRECTION

PATENT NO. : 6,541,656 B2
DATED : April 1, 2003
INVENTOR(S) : Yurugi et al.

It is certified that error appears in the above-identified patent and that said Letters Patent is hereby corrected as shown below:

Column 24,
Line 34, after "and/or" insert -- unsaturated --

Column 26,
Lines 22, 25, 29 and 33, delete "is" and insert -- in --
Line 52, delete "(6 )" and insert -- (3) --

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,541,656 B2
DATED : April 1, 2003
INVENTOR(S) : Yurugi et al.

It is certified that error appears in the above-identified patent and that said Letters Patent is hereby corrected as shown below:

Column 24,
Line 10, delete "satured" and insert -- saturated --
Line 67, before "represents" insert -- each --

Column 25,
Line 9, after "ester" insert -- group --
Line 30, delete "." and insert -- , --
Line 64, delete "am" and insert -- an --

Column 26,
Lines 16-17, delete "acrboxylic" and insert -- carboxylic --
Line 37, after "of" insert -- the --
Lines 44-45, delete "carboxylix" and insert -- carboxylic --

Signed and Sealed this

Twenty-first Day of October, 2003

JAMES E. ROGAN
*Director of the United States Patent and Trademark Office*